United States Patent
Bartholf et al.

(10) Patent No.: US 6,942,688 B2
(45) Date of Patent: Sep. 13, 2005

(54) STENT DELIVERY SYSTEM HAVING DELIVERY CATHETER MEMBER WITH A CLEAR TRANSITION ZONE

(75) Inventors: Heather A. Bartholf, Miami, FL (US); Robert F. Graham, Miami, FL (US)

(73) Assignee: Cordis Corporation, Miami Lakes, FL (US)

(*) Notice: Subject to any disclaimer, the term of this patent is extended or adjusted under 35 U.S.C. 154(b) by 0 days.

(21) Appl. No.: 09/782,444

(22) Filed: Feb. 13, 2001

(65) Prior Publication Data

US 2001/0034549 A1 Oct. 25, 2001

Related U.S. Application Data

(60) Provisional application No. 60/185,798, filed on Feb. 29, 2000.

(51) Int. Cl.[7] .................................................. A61P 2/06
(52) U.S. Cl. ........................................ 623/1.11; 606/194
(58) Field of Search ............................ 623/1.11, 1.12; 606/194, 195, 192

(56) References Cited

U.S. PATENT DOCUMENTS

| | | |
|---|---|---|
| 4,327,722 A | 5/1982 | Groshong et al. |
| 4,580,568 A | 4/1986 | Gianturco |
| 4,665,771 A | 5/1987 | Mitchell |
| 4,665,905 A | 5/1987 | Brown |
| 4,732,152 A | 3/1988 | Wallsten et al. |
| 4,773,665 A | 9/1988 | Hindle |
| 4,925,445 A | 5/1990 | Sakamoto et al. |
| 5,221,270 A * | 6/1993 | Parker ........................ 604/282 |
| 5,405,369 A | 4/1995 | Selman et al. |
| 5,545,149 A | 8/1996 | Brin et al. |
| 5,704,914 A | 1/1998 | Stocking et al. |
| 5,733,248 A | 3/1998 | Adams et al. |
| 5,833,694 A * | 11/1998 | Poncet ........................ 606/108 |
| 5,954,652 A | 9/1999 | Heyman |
| 6,019,778 A * | 2/2000 | Wilson et al. ............... 606/198 |
| 6,309,379 B1 * | 10/2001 | Willard et al. .............. 604/467 |
| 6,379,365 B1 * | 4/2002 | Diaz ........................... 606/198 |
| 6,726,712 B1 * | 4/2004 | Raeder-Devens et al. .. 623/1.11 |

FOREIGN PATENT DOCUMENTS

| | | |
|---|---|---|
| EP | 0812579 A1 | 12/1997 |
| WO | WO97/40879 A1 | 11/1997 |
| WO | WO98/23241 A2 | 6/1998 |

* cited by examiner

*Primary Examiner*—Bruce E Snow

(57) ABSTRACT

A catheter based stent placement system in which the catheter has a clear or translucent transition zone for visual inspection of the stent when placed in the catheter.

5 Claims, 2 Drawing Sheets

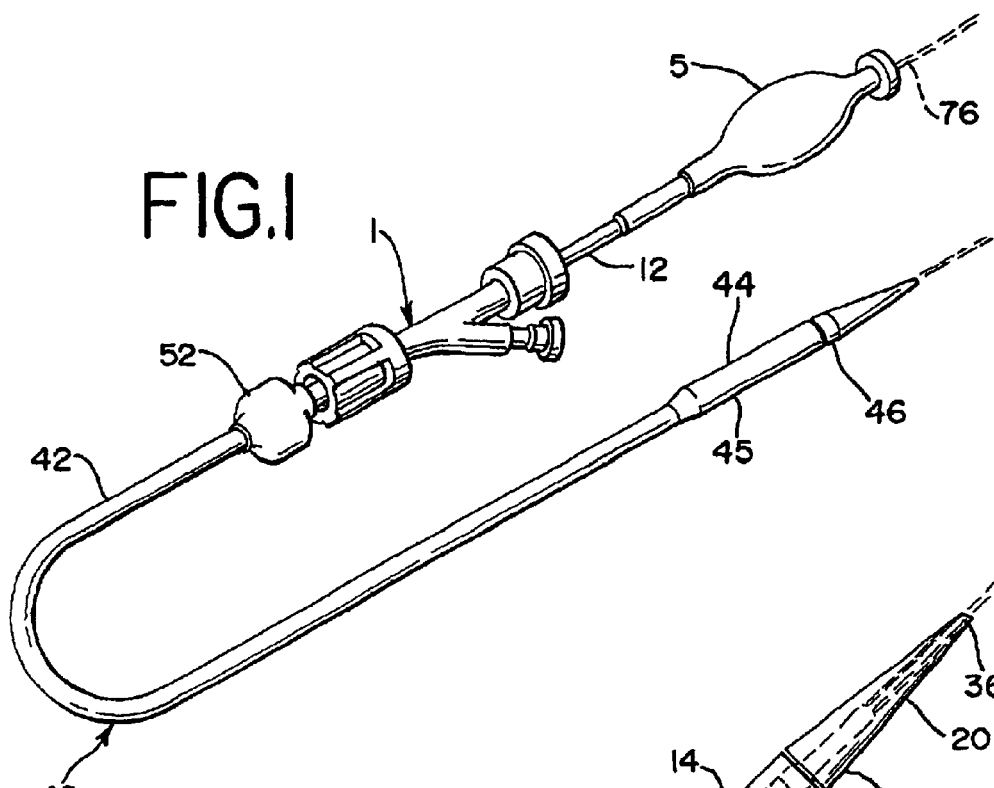
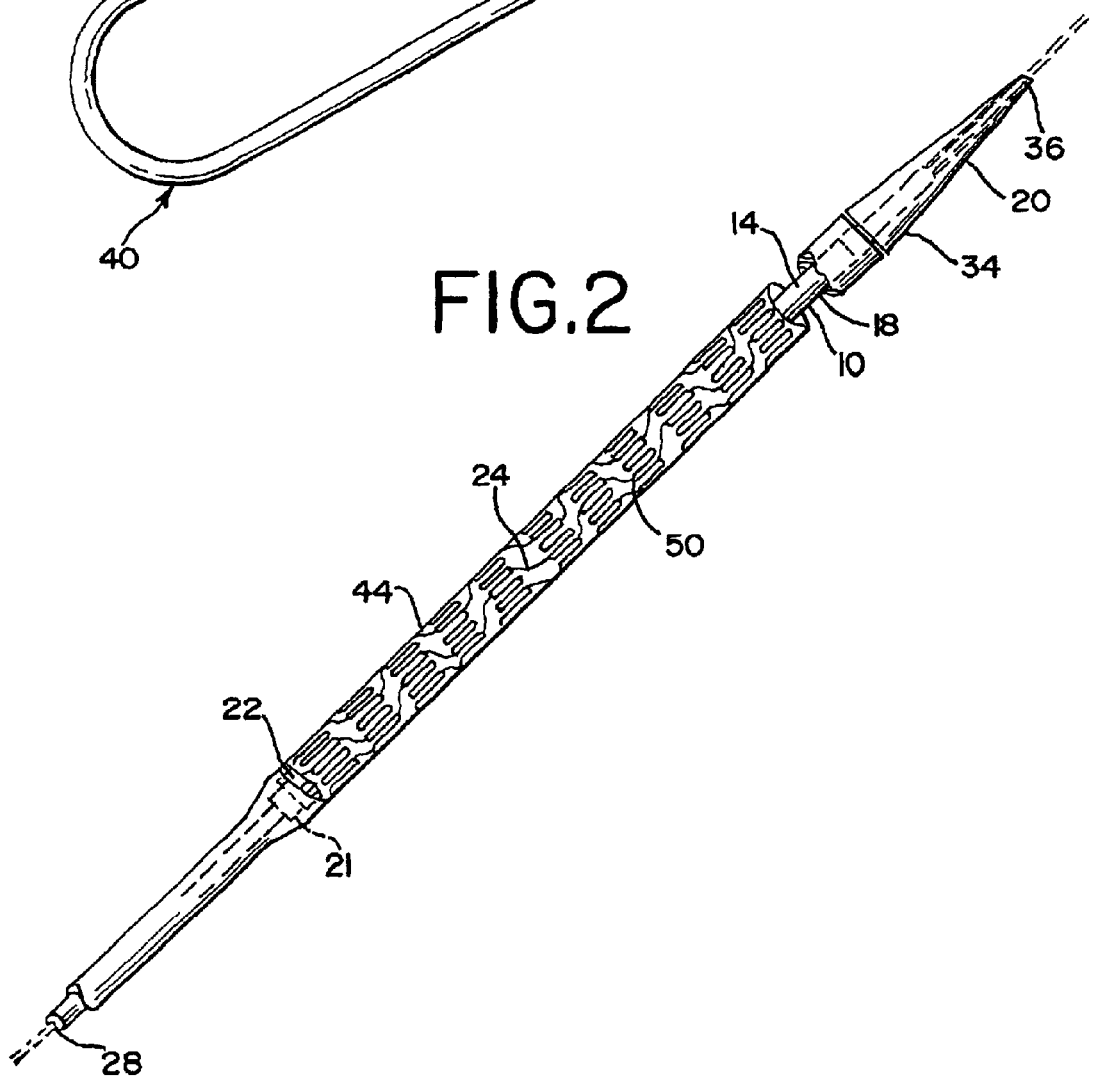

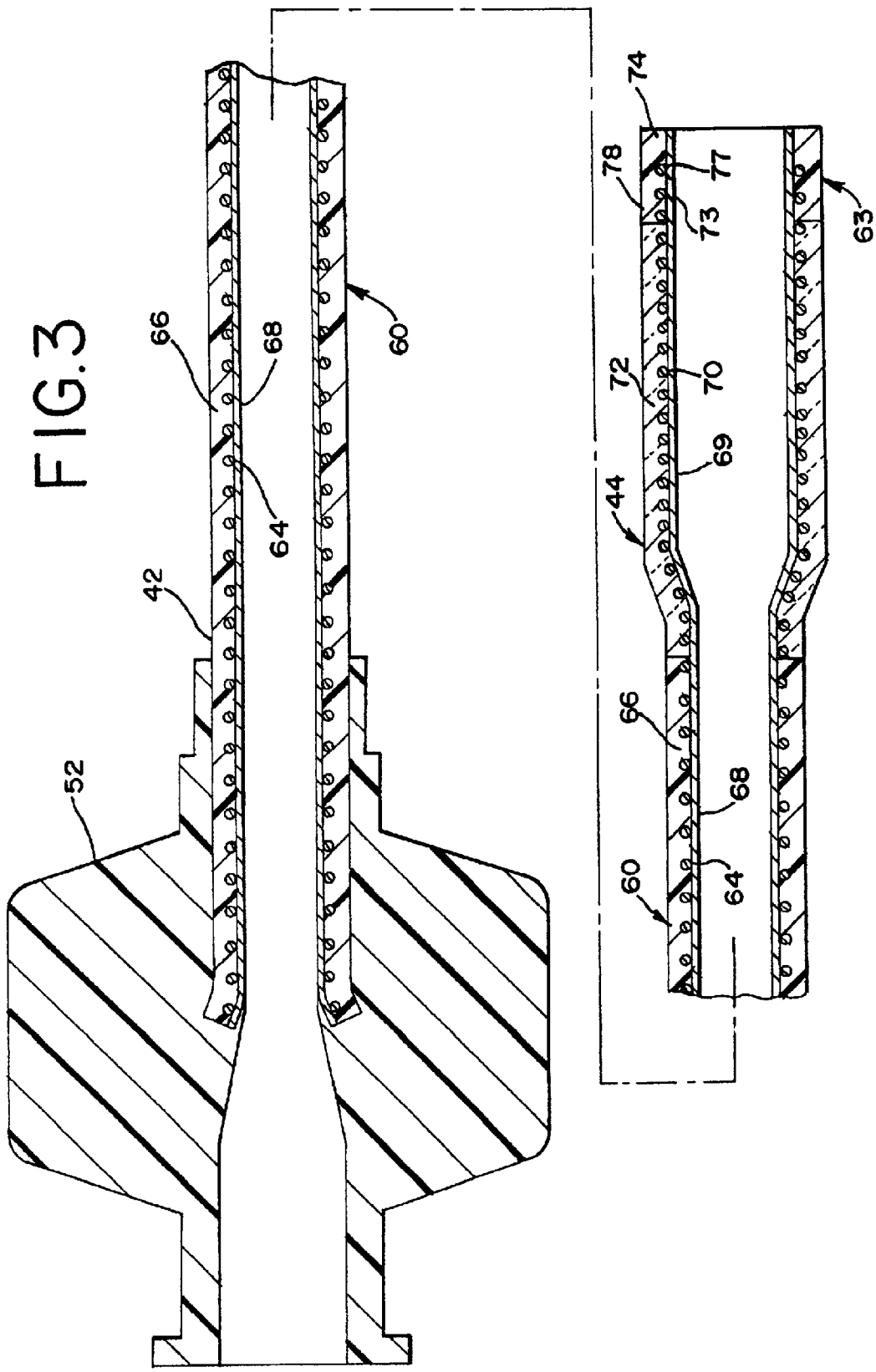

STENT DELIVERY SYSTEM HAVING DELIVERY CATHETER MEMBER WITH A CLEAR TRANSITION ZONE

This application claims benefit to provisional application 60/185,798 filed Feb. 29, 2000.

FIELD OF THE INVENTION

The present invention relates to an expandable intraluminal medical device, for example a stent, for use within a body passageway for repairing blood vessels narrowed or occluded by disease. More particularly, the present invention relates to a system for delivering such stents.

RELATED PATENT APPLICATION

The present invention is an improvement of the stent delivery system disclosed in co-pending U.S. patent application Ser. No. 09/243,750, entitled, "A Delivery Apparatus For A Self Expanding Stent," filed Feb. 3, 1999, assigned to the same assignee as the subject patent application, and hereby incorporates by reference.

BACKGROUND OF THE INVENTION

Percutaneous transluminal coronary angioplasty (PTCA) is a therapeutic medical procedure used to increase blood flow through the coronary artery and can often be used as an alternative to coronary by-pass surgery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Recently, transluminal prostheses have been widely used in the medical arts for implantation in blood vessels, bilary ducts, or other similar organs of the living body. These prostheses are commonly known as stents and are used to maintain, open, or dilate tubular structures. An example of a commonly used stent is given in U.S. Pat. No. 4,733,665 filed by Palmaz on Nov. 7, 1985, which is hereby incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly extending.

However, such stents are often impractical for use in some vessels such as the carotid artery. The carotid artery is easily accessible from the exterior of the human body, and is often visible by looking at ones neck. A patient having a balloon expandable stent made from stainless steel or the like, placed in their carotid artery might be susceptible to severe injury through day to day activity. A sufficient force placed on the patient's neck, such as by falling, could cause the stent to collapse, resulting in injury to the patient. In order to prevent this, self-expanding stents have been proposed for use in such vessels. Self-expanding stents act like springs and will recover to their expanded or implanted configuration after being crushed.

One type of self-expanding stent is disclosed in U.S. Pat. No. 4,665,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprise an outer catheter for holding the stent at its distal end, and an inner piston which pushes the stent forward once it is in position.

Other types of self-expanding stents use alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

Designing delivery systems for delivering self-expanding stents has proven difficult. One example of a prior art selfexpanding stent delivery system is shown in U.S. Pat. No. 4,580,568 issued to Gianturco on Apr. 8, 1986. This reference discloses a delivery apparatus which uses a hollow sheath, like a catheter. The sheath is inserted into a body vessel and navigated therethrough so that its distal end is adjacent the target site. The stent is then compressed to a smaller diameter and loaded into the sheath at the sheath's proximal end. A cylindrical flat end pusher, having a diameter almost equal to the inside diameter of the sheath is inserted into the sheath behind the stent. The pusher is then used to push the stent from the proximal end of the sheath to the distal end of the sheath. Once the stent is at the distal end of the sheath, the sheath is pulled back, while the pusher remains stationary, thereby exposing the stent and expanding it within the vessel.

However, delivering the stent through the entire length of the catheter can cause many problems, including possible damage to a vessel or the stent during its travel. In addition, it is often difficult to design a pusher having enough flexibility to navigate through the catheter, but also enough stiffness to push the stent out of the catheter. Therefore, it was discovered that pre-loading the stent into the distal end of the catheter, and then delivering the catheter through the vessel to the target site may be a better approach. In order to ensure proper placement of the stent within catheter, it is often preferred that the stent be pre-loaded at the manufacturing site. Except this in itself has posed some problems. Because the catheter exerts a significant force on the self-expanding stent which keeps it from expanding, the stent may tend to become imbedded within the inner wall of the catheter. When this happens, the catheter has difficulty sliding over the stent during delivery. This situation can result in the stent becoming stuck inside the catheter, or could damage the stent during delivery.

Another example of a prior art self-expanding stent delivery system is given in U.S. Pat. No. 4,732,152 issued to Wallsten et al. on Mar. 22, 1988. This patent discloses a probe or catheter having a self-expanding stent pre-loaded into its distal end. The stent is first placed within a flexible hose and compressed before it is loaded into the catheter. When the stent is at the delivery site the catheter and hose are withdrawn over the stent so that it can expand within the vessel. However, withdrawing the flexible hose over the stent during expansion could also cause damage to the stent.

For prior art delivery devices, the maximum outside diameter of the device was usually controlled by the diameter of the stent prior to deployment. Typically, the stent may only be compressed so much, and therefore its diameter is determined by the maximum diameter of the delivery device. For prior art devices, the diameter of the entire delivery device along its length is substantially uniform. Therefore, the outside diameter along the entire length of the device was its maximum diameter as required by the stent. That is, the overall outer diameter of the outer sheath for these devices is controlled by the size of the pre-loaded stent. As explained below, large sized outer sheaths can pose obstacles to the physician.

Often a sheath, such as, a guiding catheter, is used with these delivery devices as a conduit into the vasculature. Using fluoroscopy, the physician will often view the targeted site, pre-deployment and post-deployment, of the stent by injecting a radiopaque solution between the guiding catheter and the delivery device. The ability to view the image is controlled by the injection rate of the solution, which is dependent upon the amount of clearance between the guiding catheter and the outer sheath of the delivery device. A large outer sheath limits the amount of radiopaque solution which can pass through the guiding catheter, causing the physician to have a less clear image of the procedure.

Another problem associated with prior stent delivery systems is caused by the fact that prior to being inserted into the body the stent is entirely covered by an opaque delivery catheter and it is not possible for the physician to visually observe the stent prior to insertion into the body. For example, the physician is unable to visually observe the length of the stent. Often times the length of a stent is very critical to the performance of the stent depending upon the length of the obstruction. In addition, the physician is unable to visually observe the location or position of the stent with the catheter, and for that matter, the physician is unable to even visually confirm that a stent is present within the delivery catheter.

Therefore, there has been a need for a self-expanding stent delivery system which overcomes the above referenced problems associated with prior art delivery systems. Specifically, there has been a need for a self-expanding stent delivery system which allows the physician to visually observe the stent, and its characteristics, within the delivery catheter prior to insertion of the catheter within the body.

SUMMARY OF THE INVENTION

In accordance with one aspect of the present invention, there is provided a medical device delivery system for using an expandable medical device within the body which includes an outer sheath comprising an elongated tubular body member and a distal section having a proximal end bonded to the distal end of the tubular body member. In addition, the distal section formed from a clear polymeric material, such as a clear nylon material, so as to make possible the visual inspection of an implantable medical device positioned beneath or within the distal section of the outer sheath. In addition, the delivery system includes an inner shaft located coaxially within the outer sheath and an implantable medical device located within the relatively clear distal section of the outer sheath. The inner shaft serves the purpose of providing for the delivery of the medical device.

In accordance with another aspect of the present invention there is provided a medical device delivery system for a self-expanding stent which includes an outer sheath having an elongated tubular body member and enlarged distal section. The distal section has a greater inside and outside diameter than the inside and outside diameter of the tubular body member. In addition, the enlarged distal section is formed from a relatively clear polymeric material such as a clear nylon material, so that a physician may visually observe the stent within the outer sheath prior to insertion of the outer sheath within the body of a patient. Also, the delivery system includes an inner shaft located coaxially within the outer sheath, and a self-expanding stent located within the relatively clear enlarged distal section of the outer sheath. The stent is maintained in frictional contact with the interior surface of the outer sheath in order to maintain the stent in a collapsed condition. In addition, the inner shaft is connected to the stent for delivering the stent at a desired location within the body.

In accordance with still another aspect of the present invention, there is provided a medical device delivery system which includes a catheter comprising a polymeric tubular body section and a flexible distal tubular section bonded to a body section. The distal tubular section is formed from a relatively clear polymeric material so that an implantable medical device, when placed within the catheter, may be visually inspected by a physician prior to insertion of the catheter within the body of a patient.

In accordance with still another aspect of the present invention, the flexible distal tubular section has an inner diameter and an outer diameter which are smaller than the inner diameter and outer diameter, of the polymeric tubular body section.

In accordance with still another aspect of the present invention, the catheter includes a distal tip which is comprised of a polymeric formulation containing from about 20 to 75 weight percent of a radiopaque agent so that the distal tip is substantially more radiopaque than the distal tubular section and the tubular body section of the catheter.

BRIEF DESCRIPTION OF THE DRAWINGS

The foregoing and other aspects of the present invention will best be appreciated with reference to the detailed description of a preferred embodiment of the present invention shown in the accompanying drawings, wherein:

FIG. 1 is a simplified perspective view of a stent delivery system in accordance with the present invention;

FIG. 2 is a view similar to that of FIG. 1 but showing an enlarged view of the distal end of the delivery system and it includes a cut-away section to illustrate a stent loaded therein; and, FIG. 3 is a cross sectional view of the outer sheath shown in FIGS. 2 and 3 illustrated in more detail.

DETAILED DESCRIPTION OF THE INVENTION

Referring now to the Figures wherein like numerals indicate the same element throughout the views, there is shown in FIGS. 1 and 2 a self-expanding stent delivery system 1 made in accordance with the present invention. System 1 comprises inner and outer coaxial tubes. The inner tube will be referred to as the shaft 10 and the outer tube will be referred to as the sheath 40. Shaft 10 has proximal and distal ends 12 and 14 respectively. The proximal end 12 of the shaft has a Luer guidewire hub 5 attached thereto. The shaft 10 has a proximal portion which is preferably made from a relatively stiff material such as stainless steel, Nitinol, or any other suitable material known to those of ordinary skill in the art. The shaft 10 also includes a distal portion 18 which is preferably made from a co-extrusion high density polyethylene for the inner portion and polyamide for the outer portion. Other suitable materials for distal portion 18 known to those of ordinary skill in the art include polyurethane, polyamide, polyetheretheketone, and Nitinol. These materials may be utilized as single or multi-layer structures, and may also include reinforcement wires, braid wires, coils, filaments or the like.

The distal end 14 of the shaft 10 includes a distal tip 20 attached thereto. Distal tip 20 can be made from any number of materials known in the art including polyamide, polyurethane, polytetrafluoroethylene, and polyethylene including multi-layer or single layer structures. The distal tip 20 has a proximal end 34 whose diameter is substantially the same as the outer diameter of the sheath 40 which is immediately adjacent thereto. The distal tip tapers to a smaller diameter from its proximal end 34 to its distal end 36, wherein the distal end 36 of the distal tip has a diameter smaller than the inner diameter of the sheath. Tip 20 helps to prevent blood from entering the sheath 40 as the system 1 is being navigated through the body vessels. Attached to distal end 14 of the shaft 10 is a stop 22 which is proximal to the distal tip 20 and stent 50. Stop 22 can be made from any number of materials known in the art, including stainless steel, and is even more preferably made from a highly radiopaque material such as platinum, gold, tantalum, or radiopaque filled polymer. The stop can be attached to shaft 10 by mechanical or adhesive bonding, or by any other means known to those skilled in the art. Preferably, the diameter of stop 22 is large enough to make sufficient contact with the loaded stent 50 at its end without making frictional contact with the inner layer of the outer sheath 40. The stop 22 helps to "push" the stent out of the sheath during deployment, by preventing the stent from migrating proximally within the sheath 40 during retraction of the sheath for stent deployment. Proximal to stop 22 is sleeve 21, which can be made from any number of materials known to those skilled in the art including plastic. Sleeve 21 is attached to shaft 10 immediately proximal to stop 22 by any number of ways known to those skilled in the art including thermal or mechanical bonding. Sleeve 21 acts to reinforce stop 22 during deployment of the stent 50. Sleeve 21 is large enough to make sufficient contact with stop 22 in order to reinforce stop 22. However, it is also preferably small enough not to interfere with the taper of outer sheath 40 when the inner shaft 10 is inside the outer sheath 40. During deployment, the outer sheath 40 is moved in a proximal direction relative to the stationary inner shaft 10. The radiopaque stop 22 also aides in positioning the stent within the target lesion during deployment within a vessel, as is described below.

A stent bed 24 is defined as being that portion of the shaft between the distal tip 20 and the stop 22 (FIG. 2). The stent bed 24 and the stent 50 are coaxial so that the portion of shaft 18 comprising the stent bed 24 is located within the lumen of stent 50. The stent bed 24 makes minimal contact with stent 50 because of the space which exists between the inner shaft 10 and the outer sheath 40. As the stent is subjected to temperatures at the austenite phase transformation it attempts to recover to its programmed shape by moving outwardly in a radial direction within the sheath. The outer sheath 40 constrains the stent as will be explained later herein.

The shaft 10 has a guidewire lumen 28 extending along its length, where the guidewire enters through the guidewire hub 5 and exits through its distal tip 20. This construction allows the shaft 10 to receive a guidewire 76 much in the same way that a balloon angioplasty catheter receives a guidewire. Such guidewires are well known in the art and help to guide catheters and other medical devices through the vasculature of the body.

Sheath 40 is preferably a polymeric catheter and has a proximal end 42 terminating at a Luer hub 52. Sheath 40 also has a distal end 45 which terminates at the proximal end 34 of distal tip 20 of the shaft 10, when the stent 50 is in an unexpanded position as shown in FIG. 2. As will be explained below, the stent is fully deployed when the marker band 46 is proximal to radiopaque stop 22, thus indicating to the physician that it is now safe to remove the system 1 from the body.

As detailed in FIGS. 2 and 3, the distal end 45 of sheath 40 includes an enlarged section 44. Enlarged section 44 has larger inside and outside diameters than the inside and outside diameters of the sheath proximal to section 44. Enlarged section 44 houses the pre-loaded stent 50, the stop 22, sleeve 21, and the stent bed 24. Proximal to sleeve 21, the outer sheath 40 tapers proximally to a smaller size diameter. One particular advantage to this invention can best be described by referring to FIG. 3. As seen in those drawings, the reduction in the size of the outer diameter of sheath 40 proximal to enlarged section 44 results in an increase in the clearance between the delivery device 1 and a guiding catheter. The tapering of sheath 40 allows for higher injection rates of radiopaque fluid, both before and after deployment of the stent, when the enlarged section 44 is placed inside a guiding catheter.

FIG. 3 illustrates in more detail the construction of the delivery sheath which includes a tubular body section 60, which is bonded to the enlarged distal section 44, which is in turn bonded to a distal tip 63. As illustrated, the Luer hub 52 is attached to the proximal end 42 of the tubular body section 60.

More particularly, the tubular body section 60 is comprised of an inner teflon layer 68, stainless steel braiding 64 applied over the inner teflon layer 68 and a top coat 66 applied over and bonded to the stainless steel braiding 64. The top coat 66 is preferably formed of an opaque nylon material and preferably includes a very minor amount of a radiopaque agent, such as less than about 20 weight percent of a polymeric radiopaque agent, such as bismuth trioxide or bismuth subcarbonate. The tubular body section 60 is bonded, preferably by heat bonding techniques, to the enlarged distal section 44 which is formed of an inner teflon layer 69 having stainless steel braiding 70 disposed on the teflon layer 69, and a top coat 72 bonded to the stainless steel braiding 70. Top coat 72 is preferably formed from nylon material, but most importantly the enlarged distal section 44 is formed of a material which is completely clear so that a medical device to be delivered, such as an expandable stent, may be visually inspected through the side wall of the distal section 44. Preferably, the top coat 72 is formed of a clear nylon material.

The enlarged distal section 44 is then bonded preferably by use of a heat seal, to the distal tip 63. The distal tip 63 also includes an inner teflon layer 73, stainless steel braiding 77 which extends longitudinally into a portion of the distal tip 63, and a top coat 78 which is bonded to the stainless steel braiding 77. The top coat 78 is preferably formed of nylon material which includes the addition of a relatively high level of a radiopaque filler material i.e. on the order of about 20 to 75 weight percent of a polymeric radiopaque agent, such as powdered bismuth trioxide or bismuth subcarbonate, in order to provide a high level of radiopacity at the distal tip of the catheter.

The catheter used with the medical delivery system of the present invention may be formed from any flexible biocompatible material, such as a polymer material or a thin metallic material. Also, the catheter may be formed of materials of various durometer, however the top coat 72 of the enlarged distal section 44 is formed from nylon having a durometer of about 40 D, and the top coat 78, of the distal tip 63 is formed of a nylon having a durometer of about 40 D to 75 D.

With this construction, it is possible to visually inspect the implantable medical device, such as an implantable stent, from outside of the catheter to thereby confirm that the medical device is properly placed within the catheter, that the medical device is of the proper length, and that the medical device is properly seated within the enlarged distal section of the catheter. Thus, the stent may be inspected during the manufacturing process to make certain that the stent is properly seated within the catheter. In addition, a physician may inspect the catheter system to ascertain whether, in fact, a stent has been placed into the delivery catheter and may visually check the length of the stent prior to inserting the catheter into the body.

The above description of a preferred embodiment has been offered for illustrative purposes only, and is not intended to limit the scope of the invention of the application, which is as defined in the claims below:

That which is claimed is:

1. A medical device delivery system for a self-expanding stent comprising:

an outer sheath comprising an elongated tubular body and a distal section;

said sheath comprising an inner, polytetrafluoroethylene resin layer having stainless steel braiding disposed thereon, and a coating applied over and bonded to the braiding with the coating of said distal section formed from a light transmissive material;

an inner shaft located coaxially within said outer sheath, said shaft having a distal end and a proximal end;

a self-expanding stent located within said distal section of said outer sheath, said stent making frictional contact with said outer sheath, and said shaft connected to said stent for delivery of said stent;

said distal section being light transmissive whereby said stent may be visually inspected through said distal section, and further in which said distal section has a greater inside and outside diameter than the inside and outside diameter of said elongated, tubular body.

2. A medical device delivery system as defined in claim 1, wherein said sheath includes a flexible distal tip bonded to the distal section, said distal tip comprising a polymeric formulation containing from about 20 to 75 weight percent of a polymeric radiopaque agent to be substantially more radiopaque than the distal section and the elongated tubular body member.

3. A medical device delivery system as defined in claim 2, wherein said elongated tubular body member is comprised of a polymeric formulation containing less than about 20 weight percent of radiopaque agent to be substantially less radiopaque than the distal tip.

4. A medical device delivery system as defined in claim 2, wherein said distal section is comprised of a clear nylon polymer.

5. A medical device delivery system as defined in claim 4, wherein said elongated tubular body is comprised of a opaque nylon material.

* * * * *